United States Patent [19]

Bedekovic et al.

[11] Patent Number: 4,668,790

[45] Date of Patent: May 26, 1987

[54] CHROMOGENIC DIHYDROFUROPYRIDINONES

[75] Inventors: Davor Bedekovic, Therwil; Ian J. Fletcher, Magden, both of Switzerland

[73] Assignee: Ciba-Geigy Corporation, Ardsley, N.Y.

[21] Appl. No.: 449,955

[22] Filed: Dec. 15, 1982

[30] Foreign Application Priority Data

Dec. 23, 1981 [CH] Switzerland ............ 8250/81
Dec. 23, 1981 [CH] Switzerland ............ 8251/81

[51] Int. Cl.$^4$ ................................. C07D 491/048
[52] U.S. Cl. ................................ 546/116; 346/220
[58] Field of Search ....................... 546/116

[56] References Cited

U.S. PATENT DOCUMENTS

| | | | |
|---|---|---|---|
| 3,775,424 | 11/1973 | Farlier | 546/116 |
| 3,916,070 | 10/1976 | Ozutsumi et al. | 428/411 |
| 3,936,564 | 2/1976 | Miyazawa et al. | 427/145 |
| 4,046,776 | 9/1977 | Garner et al. | 544/144 |
| 4,102,893 | 7/1978 | Garner et al. | 106/14.5 |
| 4,334,072 | 6/1982 | Becker et al. | 546/112 |
| 4,564,679 | 1/1986 | Fujino et al. | 546/116 |

FOREIGN PATENT DOCUMENTS

| | | |
|---|---|---|
| 2445333 | 12/1979 | France . |
| 49-118515 | 11/1974 | Japan . |
| 05116 | 1/1975 | Japan . |
| 50-3426 | 1/1975 | Japan . |
| 1443617 | 7/1976 | United Kingdom . |
| 2006248 | 5/1979 | United Kingdom . |
| 2031934 | 3/1980 | United Kingdom . |
| 2075042 | 11/1981 | United Kingdom . |

*Primary Examiner*—Henry R. Jiles
*Assistant Examiner*—Bernard I. Dentz
*Attorney, Agent, or Firm*—Edward McC. Roberts; Meredith C. Findlay; Kevin T. Mansfield

[57] ABSTRACT

Chromogenic dihydrofuropyridinones of the general formula

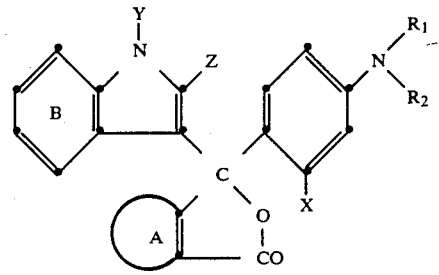

wherein $R_1$ and $R_2$ independently of each other are hydrogen, $C_1$–$C_{12}$ alkyl which is unsubstituted or substituted by halogen, hydroxyl, cyano or lower alkoxy, or are cycloalkyl, benzyl or phenyl, or benzyl or phenyl which are substituted by halogen, nitro, lower alkyl or lower alkoxy; or $R_1$ and $R_2$ together with the nitrogen atom to which they are attached are pyrrolidinyl;

X is hydrogen, halogen, lower alkyl, lower alkoxy, benzyl, phenyl, benzyloxy, phenoxy, or benzyl or benzyloxy which are substituted by halogen, nitro, lower alkyl or lower alkoxy;

Y is $C_6$–$C_9$alkyl;

Z is hydrogen, lower alkyl or phenyl; and the ring A is a pyridine radical and the benzene nucleus B is unsubstituted or substituted by halogen, nitro, lower alkyl, lower alkoxy, amino or lower alkylamino.

These compounds are useful color formers for pressure-sensitive or heat-sensitive recording materials and produce, in particular, strong, lightfast blue colorations.

8 Claims, No Drawings

CHROMOGENIC DIHYDROFUROPYRIDINONES

The present invention relates to chromogenic dihydrofuropyridinones, to the preparation thereof, and to the use thereof as colour formers in pressure-sensitive or heat-sensitive recording materials.

The chromogenic dihydrofuropyridinones of this invention have the general formula

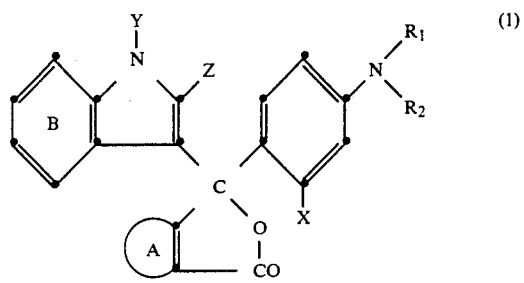

wherein
- $R_1$ and $R_2$ independently of each other are hydrogen, $C_1$–$C_{12}$alkyl which is unsubstituted or substituted by halogen, hydroxyl, cyano or lower alkoxy, or are cycloalkyl, benzyl or phenyl, or benzyl or phenyl which are substituted by halogen, nitro, lower alkyl or lower alkoxy; or $R_1$ and $R_2$ together with the nitrogen atom to which they are attached are pyrrolidinyl;
- X is hydrogen, halogen, lower alkyl, lower alkoxy, benzyl, phenyl, benzyloxy, phenoxy, or benzyl or benzyloxy which are substituted by halogen, nitro, lower alkyl or lower alkoxy;
- Y is $C_6$–$C_9$alkyl;
- Z is hydrogen, lower alkyl or phenyl; and
- the ring A is a pyridine radical and
- the benzene nucleus B may be further substituted by halogen, nitro, lower alkyl, lower alkoxy, amino or lower alkylamino.

In the definition of the radicals of the dihydrofuropyridinones, the term "lower" qualifying alkyl and alkoxy groups will normally be understood to denote groups which contain 1 to 5, preferably 1 to 3, carbon atoms. Examples of lower alkyl groups are methyl, ethyl, n-propyl, isopropyl, n-butyl, sec-butyl or amyl, and examples of lower alkoxy groups are methoxy, ethoxy or isopropoxy.

$R_1$ and $R_2$ as alkyl group may be straight chain or branched alkyl groups, e.g., methyl, ethyl, n-propyl, isopropyl, n-butyl, sec-butyl, amyl, n-hexyl, n-octyl or n-dodecyl.

$R_1$ and $R_2$ are substituted alkyl groups are in particular cyanoalkyl, haloalkyl, hydroxyalkyl, alkoxyalkyl, each containing preferably a total of 2 to 4 carbon atoms, e.g. β-cyanoethyl, β-chloroethyl, β-hydroxyethyl, β-methoxyethyl or β-ethoxyethyl.

$R_1$ and $R_2$ as cycloalkyl may be cyclopentyl or, preferably, cylohexyl.

Preferred substituents in the benzyl moiety of the radicals R and X, in the phenyl moiety of the radicals $R_1$ and $R_2$ and in the benzyloxy moiety of the radical X are e.g. halogens, nitro, methyl or methoxy.

Examples of such araliphatic and aromatic radicals are p-methylbenzyl, o- or p-chlorobenzyl, o- or p-nitrobenzyl, o- or p-tolyl, xylyl, o-, m- or p-chlorophenyl, o- or p-nitrophenyl, o- or p-methoxyphenyl, chlorobenzyloxy or methylbenzyloxy.

The substituents $R_1$ and $R_2$ are preferably benzyl or, most preferably, lower alkyl. $R_1$ and $R_2$ together with the nitrogen atom to which they are attached can form a pyrrolidinyl radical, which is also a preferred substituent. $R_1$ is advantageously also cyclohexyl.

X may be with advantage hydrogen, halogen, lower alkyl, e.g. methyl; or benzyloxy or lower alkoxy, e.g. methoxy, ethoxy, isopropoxy or tert-butoxy. X is preferably hydrogen, benzyloxy or lower alkoxy, and is most preferably ethoxy.

An alkyl radical Y may be n-hexyl, 2-ethylhexyl, n-heptyl, n-octyl, isooctyl, tert-octyl, n-nonyl or isononyl. The N-substituent Y is preferably $C_6$–$C_8$alkyl, e.g. n-hexyl, n-heptyl or, most preferably, n-octyl. Z is preferably phenyl or, most preferably, methyl.

The nitrogen atom of the pyridine ring A is advantageously in the ortho-position to the carbonyl group or in the ortho-position to the linking carbon atom of the furan ring. The chromagenic dihydrofuropyridinones of this invention are preferably mixtures of isomers of 5,5-disubstituted 5,7-dihydrofuro-7-pyridinones and 7,7-disubstituted 5,7-dihydrofuro-5-pyridinones, in which the nitrogen atoms of the pyridine ring are in the ortho-positions specified above. The ring B is preferably not further substituted or may also be substituted by halogen.

Interesting chromogenic dihydrofuropyridinones are those of the formula

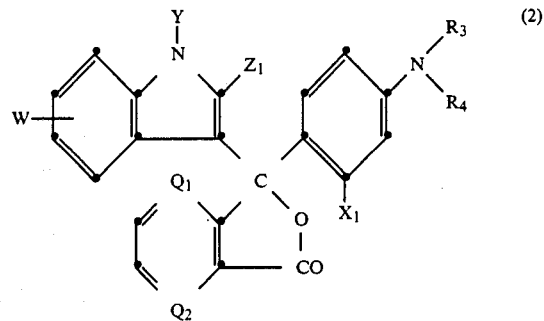

wherein $R_3$ and $R_4$ independently of each other are lower alkyl, benzyl, or benzyl which is substituted by halogen, methyl or methoxy, or $R_3$ and $R_4$ together with the nitrogen atom to which they are attached are pyrrolidinyl; one of $Q_1$ and $Q_2$ is nitrogen and the other is CH, $X_1$ is hydrogen, lower alkoxy or benzyloxy; Y is $C_6$–$C_9$alkyl, $Z_1$ is lower alkyl or phenyl; and W is hydrogen or halogen.

Halogen in connection with the above substituents in formulae (1) and (2) denotes e.g. fluorine, bromine or preferably chlorine.

Preferred dihydrofuropyridinones of the formula (2), which are obtained preferably in the form of mixtures of isomers, are those in which $X_1$ is lower alkoxy and Y is $C_6$–$C_8$alkyl, in particular n-octyl. $R_3$ and $R_4$ are preferably lower alkyl.

Particularly interesting mixtures of isomers are those of dihydrofuropyridinones of the formula

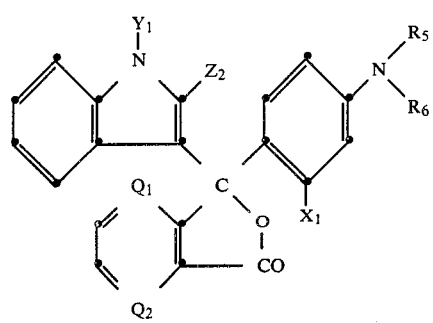

wherein each of $R_5$ and $R_6$ is lower alkyl or benzyl, or $R_5$ and $R_6$ together with the nitrogen atom to which they are attached are pyrrolidinyl; one of $Q_1$ and $Q_2$ is N and the other is CH; $X_1$ is hydrogen, benzyloxy or lower alkoxy, preferably ethoxy; $Z_2$ is methyl or phenyl; and $Y_1$ is $C_6$–$C_8$alkyl, preferably, n-hexyl or, most preferably, n-octyl.

Particularly preferred compounds of the formula (3) are those in which $R_5$ and $R_6$ are methyl or ethyl, or $R_5$ and $R_6$ together with the nitrogen atom to which they are attached are pyrrolidinyl, and $X_1$ is ethoxy, $Z_2$ is methyl and $Y_1$ is n-octyl.

The dihydrofuropyridinones of the formulae (1) to (3) are novel compounds and may be prepared by methods which are known per se. One process for the preparation of the dihydrofuropyridinones of the formula (1) comprises reacting a compound of the formula

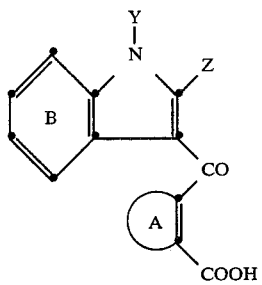

with a compound of the formula

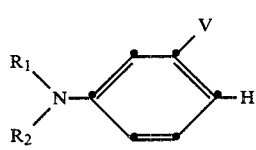

in which formulae above A, B, Y, Z, $R_1$ and $R_2$ have the meanings previously assigned to them and V has the meaning of X or is hydroxy, and subsequently alkylating or aralkylating the reaction product if V is hydroxy.

Alternatively, the dihydrofuropyridinones of the invention may also be prepared by reacting a compound of the formula

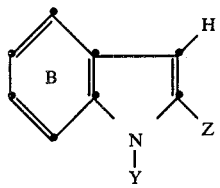

with an indole of the formula

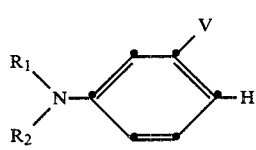

in which formulae above A, B, $R_1$, $R_2$, Y and Z have the meanings previously assigned to them and V has the meaning of X or is hydroxy, and subsequently alkylating or aralkylating the reaction product if V is hydroxy.

The above processes are preferably carried out by reacting the reaction components in the presence of an acid condensing agent in the temperature range from 20° to 80° C. Examples of such condensing agents are acetic anhydride, sulfuric acid, zinc chloride and phosphoroxy chloride.

The alkylation or aralkylation of the reaction products in which V is hydroxy, is ordinarily carried out by known methods. For example, the reaction is carried out in the presence of an acid acceptor, e.g. an alkali metal carbonate, or a tertiary nitrogen base such as triethylamine, and optionally in the presence of an inert organic solvent such as acetone, isopropyl alcohol, chlorobenzene or nitrobenzene. Suitable alkylating agents are alkyl halides such as methyl iodide, ethyl iodide, methyl chloride or ethyl chloride, or dialkyl sulfates such as dimethyl sulfate or diethyl sulfate. Suitable aralkylating agents are in particular benzyl chloride and the corresponding substitution products, e.g. p-chlorobenzyl chloride or 2,4-dimethylbenzyl chloride, which are preferably used in a non-polar organic solvent such as benzene, toluene or xylene.

The starting materials of the formulae (4) and (6) are normally obtained by reacting an anhydride of the formula

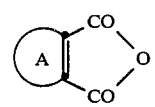

with a compound of the formula (7) or with a compound of the formula (5), said reaction being carried out, if desired, in an organic solvent and optionally in the presence of a Lewis acid, e.g. aluminium chloride. Examples of suitable organic solvents are: dimethylformamide, acetonitrile, lower aliphatic carboxylic acids such as acetic acid; and benzene, toluene, xylene or chlorobenzene. It is preferred to carry out the reaction in the temperature range from 15° C. to the boiling point of the solvent employed. Without being isolated, the resultant compounds of the formula (4) may be further used for the reaction with the aniline compounds of the formula (5). The compounds of the formula (6), wherein V is alkoxy or benzyloxy, are preferably obtained by conventional alkylation or aralkylation of the intermediate obtained by reacting an anhydride of the formula (8) with an aniline compound of the formula (5), wherein V is hydroxy. The alkylating and aralkylating agents may be the same as those indicated for the preparation of the compounds of the formulae (1) to (3).

The dihydrofuropyridinones of the formulae (1) to (3) are normally colourless or, at most, faintly coloured. When these colour formers are brought into contact with an acid developer, e.g. an electron acceptor, they produce intense greenish blue, blue or violet blue shades of excellent fastness to sublimation and light. They are therefore also very useful when mixed with one or more other known colour formers, for example 3,3-(bis-aminophenyl)-phthalides, 3,3-(bis-indolyl)-phthalides, 3-aminofluoranes, 2,6-diaminofluoranes, leucoauramines, spiropyranes, spirodipyranes, chromenoindoles, phenoxazines, phenothiazines, carbazolylmethanes or triarylmethane-leuco dyes, to give blue, navy blue, grey or black colorations.

The dihydrofuropyridinones of the formulae (1) to (3) exhibit both on clays and especially on phenolic substrates an improved colour intensity and lightfastness. They are suitable in particular as rapidly developing colour formers for use in a heat-sensitive or especially in a pressure-sensitive recording material which can also be a copying material.

A pressure-sensitive material consists, for example, of at least one pair of sheets which contain at least one colour former of the formulae (1) to (3) dissolved in an organic solvent, and a solid electron acceptor as developer.

Typical examples of such developers are activated clays such as attapulgite, acid clay, bentonite, montmorillonite, activated clay, e.g. acid-activated bentonite or montmorillonite, and also zeolith, halloysite, silica, alumina, aluminium sulfate, aluminium phosphate, zinc chloride, kaolin or any clay. Preferred developers are acidic organic compounds, for example unsubstituted or ring-substituted phenols, salicylic acid or salicylates and their metal salts, or an acidic polymer, for example a phenolic polymer, an alkylphenolacetylene resin, a maleic acid/rosin resin or a partially or completely hydrolysed polymer of maleic acid and styrene, ethylene or vinyl methyl ether, or carboxypolymethylene. Mixtures of these polymers can also be used. Particularly preferred developers are zinc salicylates or the condensation products of p-substituted phenols with formaldehyde. These latter may also contain zinc.

The developers may also be used with other basically inert or almost inert pigments. Examples of such pigments are: talcum, titanium dioxide, zinc oxide, chalk, clays such as kaolin, as well as organic pigments, e.g. urea/formaldehyde or melamine/formaldehyde condensates.

The colour former effects a coloured marking at those points where it comes into contact with the electron acceptor. In order to prevent the colour formers contained in the pressure-sensitive recording material from becoming active prematurely, they are usually separated from the electron acceptor. This separation can conveniently be accomplished by incorporating the colour formers in foamlike, spongelike or honeycomb-like structures. Preferably, the colour formers are enclosed in microcapsules, which as a rule can be ruptured by pressure.

When the capsules are ruptured by pressure, for example with a pencil, and the colour former solution is transferred in this manner to an adjacent sheet which is coated with an electron acceptor, a coloured area in produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a polyhalogenated paraffin, such as chloroparaffin, or a polyhalogenated diphenyl, such as monochlorodiphenyl or trichlorodiphenyl, and also tricresyl phosphate, di-n-butyl phthalate, dioctyl phthalate, trichlorobenzene, trichloroethylphosphate, an aromatic ether such as benzylphenyl ether, a hydrocarbon oil such as paraffin or kerosene, an alkylated (e.g. with isopropyl, isobutyl, sec- or tert-butyl) derivative of diphenyl, naphthalene or triphenyl; dibenzyl toluene, terphenyl, partially hydrogenated terphenyl, a monobenzylated and/or dibenzylated xylene, a mono- or tetramethylated diphenylalkane, e.g. bis-tolylethane or bis-xylylethane, 1-isopropylphenyl-2-phenylethane or bis-(isopropylphenyl)ethane; or other chlorinated or hydrogenated, condensed aromatic hydrocarbons. Mixtures of different solvents, especially mixtures of paraffin oils or kerosene and diisopropylnaphthalene or partially hydrogenated terphenyl, are often used in order to obtain an optimum solubility for the colour formation, a rapid and intense coloration, and a viscosity which is advantageous for the microencapsulation. In this regard, the dihydrofuropyridinones of this invention have the property that, on account of the long chain N-alkyl radical of Y, they remain colourless in the solutions of the above solvents, especially diisopropylnaphthalene or partially hydrogenated terphenyl, in a pH range from 4 to 10, and thus do not stain the aqueous phase, e.g. during encapsulation.

The capsule walls can be formed evenly around the droplets of the colour former solution by coacervation; and the encapsulating material can consist of gelatin and gum arabic, as described e.g. in U.S. Pat. No. 2,800,457. The capsules can also be formed preferably from an aminoplast or a modified aminoplast by polycondensation, as described in British patent specifications 989 264, 1 156 725, 1 301 052 and 1 355 124. Also suitable are microcapsules which are formed by interfacial polymerisation, e.g. capsules formed from polyester, polycarbonate, polysulfonamide, polysulfonate, but in particular from polyamide or polyurethane.

The microcapsules containing the colour formers of the formulae (1) to (3) can be used for the production of a wide variety of known kinds of pressure-sensitive copying material. The various systems differ substantially from one another in the arrangement of the capsules, the colour reactants, i.e. the developers, and/or the support. A preferred arrangement is that in which the encapsulated colour former is in the form of a layer on the back of a transfer sheet and the developer is in the form of a layer on the face of a receiver sheet.

Another arrangement of the components is that wherein the microcapsules which contain the colour former, and the developer, are in or on the same sheet, in the form of one or more individual layers, or are present in the paper pulp.

The capsules are preferably secured to the support by means of a suitable adhesive. As paper is the preferred support, these adhesives are principally paper-coating agents, for example gum arabic, polyvinyl alcohol, hydroxymethyl cellulose, casein, methyl cellulose, dextrin, starch or starch derivatives or polymer latices. These latter are e.g. butadiene/styrene copolymers or acrylic homopolymers or copolymers.

The paper employed comprises not only normal paper made from cellulose fibres, but also paper in which the cellulose fibres are replaced (partially or completely) by synthetic polymers.

The compounds of the formulae (1) to (3) can also be employed as developers in a thermoreactive recording material. This recording material usually contains at least one carrier, one colour former, one electron acceptor and, optionally, also a binder. Thermoreactive recording systems comprise, for example, heat-sensitive recording and copying materials and papers. These systems are used e.g. for recording information, for example in electronic computers, teleprinters or telewriters, or in recording and measuring instruments, e.g. electrocardiographs. The image (mark) formation can also be effected manually with a heated pen. Laser beams can also be used to produce heat-induced marks.

The thermoreactive recording material can be composed such that the colour former is dispersed or dissolved in one binder layer and the developer is dissolved or dispersed in the binder in a second layer. Another possibility consists in dispersing both the colour former and the developer in one layer. By means of heat the binder is softened at specific areas and the colour former comes into contact with the developer (electron acceptor) at those points where heat is applied and the desired colour develops at once.

Suitable developers are the same electron acceptors as are used in pressure-sensitive papers. Examples of developers are the clays already mentioned and especially phenolic resins, or also the phenolic compounds described e.g. in German Offenlegungsschrift 1 251 348, for example 4-tert-butylphenol, 4-phenylphenol, 4-hydroxydiphenyl ether, α-naphthol, β-naphthol, 4-hydroxymethylbenzoate, 4-hydroxyacetophenone, 2,2'-dihydroxydiphenyl, 4,4-isopropylidenediphenol, 4,4'-isopropylidene-bis-(2-methylphenol), 4,4'-bis-(hydroxyphenyl) valeric acid, 2,2'-methylene-bis-(4-phenylphenol), hydroquinone, pyrogallol, phloroglucinol, p-, m- and o-hydroxybenzoic acid, gallic acid, 1-hydroxy-2-naphthoic acid, as well as boric acid or organic, preferably aliphatic, dicarboxylic acids, for example tartaric acid, oxalic acid, maleic acid, citric acid, citraconic acid or succinic acid.

Fusible, film-forming binders are preferably used for the manufacture of the thermoreactive recording material. These binders are normally water-soluble, whereas the dihydrofuropyridinones and the developer are reluctantly soluble or insoluble in water. The binder should be able to disperse and fix the colour former and the developer at room temperature.

By applying heat the binder softens or melts, so that the colour former comes in contact with the developer and a colour is able to form. Examples of binders which are soluble, or at least swellable, in water are e.g. hydrophilic polymers, for example polyvinyl alcohol, polyacrylic acid, hydroxyethyl cellulose, methyl cellulose, carboxymethyl cellulose, polyacrylamide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose and polyvinyl carbazole. The preferred arrangement, however, is that in which the colour former and the developer are contained in one layer in a water-soluble binder.

The thermoreactive coatings can contain further ingredients. To improve the degree of whiteness, to facilitate the printing of papers, and to prevent the heated pen from sticking, the coatings can contain e.g. talcum, titanium dioxide, zinc oxide, aluminium hydroxide, calcium carbonate (e.g. chalk), clays or also organic pigments, for example urea/formaldehyde polymers. In order to effect the colour formation only within a limited temperature range, it is possible to add substances such as urea, thiourea, diphenyl thiourea, acetamide, acetanilide, stearyl amide, phthalic anhydride, metal stereates, phthalonitrile or other appropriate fusible products which induce the simultaneous melting of the colour former and the developer. Thermographic recording materials preferably contain waxes, e.g. carnauba wax, montan wax, paraffin wax or polyethylene wax.

The invention is illustrated by the following Examples, in which percentages are by weight, unless otherwise indicated.

EXAMPLE 1

60 g of quinolinic anhydride and 116 g of 1-n-octyl-2-methylindole are stirred for $3\frac{1}{2}$ hours at 65°–70° C. in 100 ml of toluene. The reaction mixture is then evaporated to dryness and the residue is dissolved at 70° C. in 2 liters of ethanol. The solution is cooled to 0° C. and the product precipitates. The precipitate is isolated by filtration, washed with ethanol and petroleum ether and dried in vacuo at 60° C., affording 90 g (57% of theory) of a mixture of isomers consisting of the compounds of the formulae

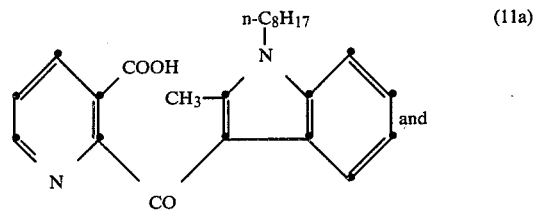

(11a)

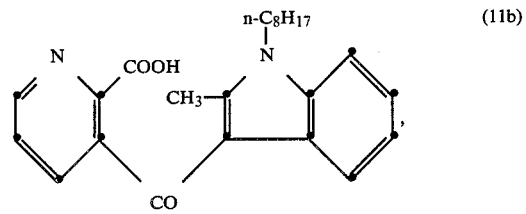

(11b)

Melting point of the mixture: 105°–112° C.

39.3 g of this mixture of isomers and 19.3 g of 3-diethylaminophenetol are stirred in 130 ml of acetic anhydride for $3\frac{1}{2}$ hours at 60°–65° C. The reaction mixture is then poured into 1 liter of water and the pH is adjusted to 8 by stirring in 30% sodium hydroxide solution. The precipitated oil is separated and dissolved in toluene.

The toluene solution is dried over sodium sulfate and concentrated. The oily residue is chromatographed through a column of alumina with a 1:1 mixture of chloroform and methanol. Yield: 30 g (53% of theory) of a mixture of isomers consisting of compounds of the formulae

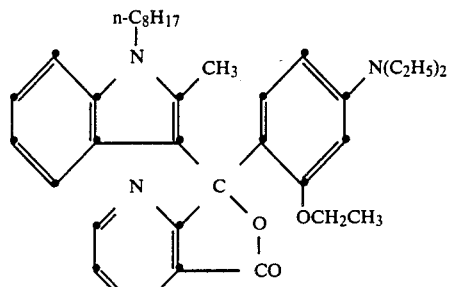
(12a)

and

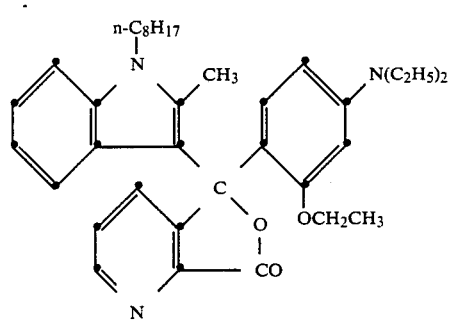
(12b)

with a melting point of 119°–121° C. This colour former develops a blue colour on phenolic resin.

Mixtures of isomers of the dihydrofuropyridinones of the formulae

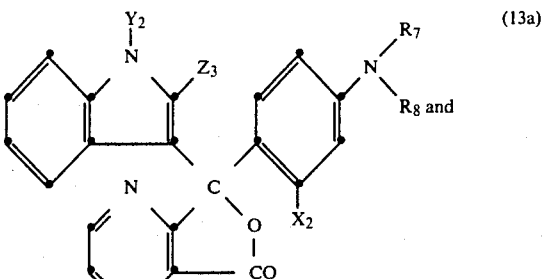
(13a)

and

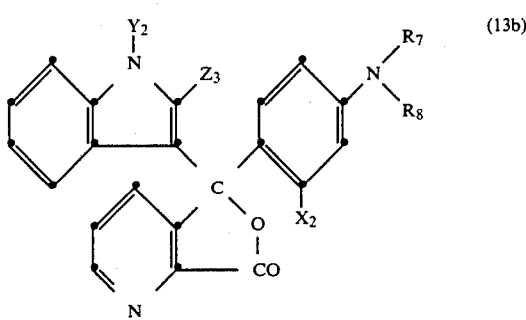
(13b)

are obtained in the same manner as described in Example 1, using the corresponding starting materials.

TABLE

| Example | $-N\begin{matrix}R_7\\R_8\end{matrix}$ | $X_2$ | $Y_2$ | $Z_3$ | p./°C. | Colour on phenolic resin |
|---|---|---|---|---|---|---|
| 2 | $-N(C_2H_5)_2$ | $-OC_2H_5$ | $-n-C_6H_{13}$ | $-CH_3$ | 134–136 | blue |
| 3 | $-N(CH_3)_2$ | H | $-n-C_8H_{17}$ | $-CH_3$ | 126–128 | blue |
| 4 | $-N(C_2H_5)_2$ | $-OC_2H_5$ | $-n-C_7H_{15}$ | $-CH_3$ | 109–113 | blue |
| 5 | $-N(C_2H_5)_2$ | $-OC_2H_5$ | $-n-C_9H_{19}$ | $-CH_3$ | 105–107 | blue |
| 6 | $-N(C_2H_5)_2$ | $-OCH_2-\text{C}_6\text{H}_5$ | $-n-C_8H_{17}$ | $-CH_3$ | 166–167 | blue |
| 7 | pyrrolidino | $-OC_2H_5$ | $-n-C_6H_{13}$ | $-CH_3$ | 146–148 | blue |
| 8 | pyrrolidino | $-OC_2H_5$ | $-n-C_7H_{15}$ | $-CH_3$ | 151–153 | blue |
| 9 | pyrrolidino | $-OC_2H_5$ | $-n-C_8H_{17}$ | $-CH_3$ | 147–148 | blue |
| 10 | pyrrolidino | $-OC_2H_5$ | $-n-C_9H_{19}$ | $-CH_3$ | 115–118 | blue |

TABLE-continued

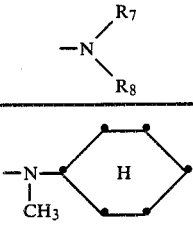

| Example | -N(R7)(R8) | X2 | Y2 | Z3 | p./°C. | Colour on phenolic resin |
| --- | --- | --- | --- | --- | --- | --- |
| 11 | -N(CH3)-[C6H4-H] | -OC2H5 | -n-C8H17 | -CH3 | 110-120 | blue |

Preparation of a pressure-sensitive copying paper

EXAMPLE 12

A solution of 3 g of the mixture of isomers of the dihydrofuropyridinones of the formulae (12a) and (12b) obtained in Example 1 in 80 g of diisopropylnaphthalene and 17 g of kerosene are microencapsulated by coacervation in a manner known per se with gelatin and gum arabic. The microcapsules are mixed with starch solution and coated on a sheet of paper. The face of a second sheet of paper is coated with phenolic resin as colour developer. The first sheet and the sheet coated with the developer are laid on top of each with other with the coated sides face to face. Pressure is exerted on the first sheet by writing by hand or typewriter and an intense blue copy of excellent lightfastness develops immediately on the sheet coated with the developer.

Correspondingly intense and lightfast blue copies are also obtained by using each of the other colour formers as obtained in Preparatory Examples 2 to 11.

EXAMPLE 13

1 g of the mixture of isomers of the dihydrofuropyridinones of the formulae (12a) and (12b) is dissolved in 17 g of toluene. With stirring, 12 g of polyvinyl acetate, 8 g of calcium carbonate and 2 g of titanium dioxide are added to this solution. The resultant suspension is diluted with toluene in the weight ratio 1:1 and applied to a sheet of paper with a knife to a thickness of 10 μm. On this sheet of paper is laid a second sheet, the underside of which has been coated to a weight of 3 g/m² with a mixture consisting of 1 part of an amide wax, 1 part of a stearic wax and 1 part of zinc chloride. Pressure is exerted on the top sheet by hand or typewriter and an intense and lightfast blue copy develops immediately on the sheet coated with the colour former.

Preparation of a heat-sensitive recording material

EXAMPLE 14

In a ball mill, 32 g of 4,4'-isopropylidenediphenol (bisphenol A), 3.8 g of the distearylamide of ethylenediamine, 39 g of kaolin, 20 g of an 88% hydrolysed polyvinyl alcohol and 500 ml of water are ground to a particle size of about 5 μm. In a second ball mill, 6 g of the mixture of isomers of the dihydrofuropyridinones of the formulae (12a) and (12b) of Example 1, 3 g of a 88% hydrolysed polyvinyl alcohol and 60 ml of water are ground to a particle size of about 3 μm.

Both dispersions are mixed and applied to paper to a dry coating weight of 5.5 g/m². An intense blue colour of excellent fastness to light and sublimation is produced by contacting the paper with a heated ball-point pen.

Intense and lightfast blue colorations are also obtained by using each of the other colour formers of Examples 2 to 11.

EXAMPLE 15

In a ball mill, 2.7 g of the mixture of isomers of the dihydrofuropyridinones of the formulae (12a) and (12b), 24 g of N-phenyl-N'-(hydroxy-2,2,2-trichloroethyl-)urea, 16 g of stearylamide, 59 g of an 88% hydrolysed polyvinyl alcohol and 58 ml of water are ground to a particle size of 2-5 μm. This suspension is applied to a sheet of paper to a dry coating weight of 5.5 g/m². An intense and lightfast blue colour is obtained by contacting the paper with a heated ball-point pen.

What is claimed is:

1. A chromogenic dihydrofluropyridinone of the formula

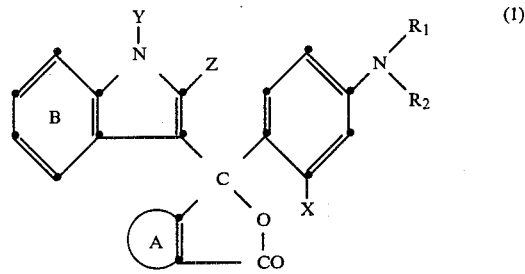

wherein
$R_1$ and $R_2$ independently of each other are lower alkyl, or benzyl;
X is hydrogen, halogen, lower alkyl, lower alkoxy, benzyl, phenyl, benzyloxy, phenoxy, or benzyl or benzyloxy which are substituted by halogen, nitro, lower alkyl or lower alkoxy;
Y is $C_6-C_9$ alkyl;
Z is hydrogen, lower alkyl or phenyl; and
the ring A is a pyridine radical and
the benzene nucleus B is unsubstituted or substituted by halogen, nitro, lower alkyl, lower alkoxy, amino or lower alkylamino.

2. A dihydrofuropyridinone according to claim 1, wherein X is hydrogen, benzyloxy or lower alkoxy.

3. A dihydrofuropyridinone according to claim 1 of the formula

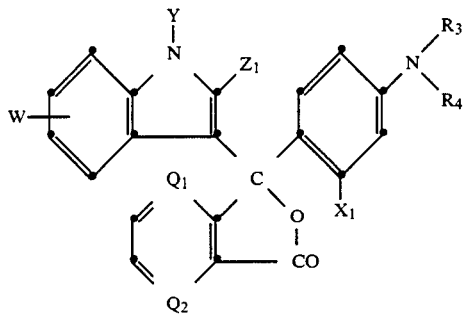

(2)

wherein $R_3$ and $R_4$ independently of each other are lower alkyl or benzyl;

one of $Q_1$ and $Q_2$ is nitrogen and the other is CH;

$X_1$ is hydrogen, lower alkoxy or benzyloxy;

Y is $C_6$-$C_9$alkyl;

$Z_1$ is lower alkyl or phenyl; and

W is hydrogen or halogen.

4. A dihydrofuropyridinone according to claim 3, wherein each of $R_3$ and $R_4$ is lower alkyl or benzyl, one of $Q_1$ and $Q_2$ is N and the other is CH, $X_1$ is hydrogen, benzyloxy or lower alkoxy, $Z_1$ is methyl or phenyl, Y is $C_6$-$C_8$alkyl and W is hydrogen.

5. A dihydrofuropyridinone according to claim 4, wherein $X_1$ is lower alkoxy.

6. A dihydrofuropyridinone according to claim 4, wherein $R_3$ and $R_4$ are methyl or ethyl, $X_1$ is ethoxy, $Z_1$ is methyl and Y is n-octyl.

7. A dihydrofuropyridinone according to claim 4, wherein $R_3$ and $R_4$ are ethyl, $X_1$ is ethoxy, $Z_1$ is methyl and Y is n-octyl.

8. A dihydrofuropyridinone according to claim 7 wherein $Q_1$ is nitrogen and $Q_2$ is CH.

* * * * *